United States Patent [19]

Meyers

[11] 4,416,296
[45] Nov. 22, 1983

[54] COMPOSITION AND METHOD FOR HAIR TREATMENT

[75] Inventor: William E. Meyers, Helena, Ala.

[73] Assignee: Carson Products Company, Savannah, Ga.

[21] Appl. No.: 207,437

[22] Filed: Nov. 17, 1980

[51] Int. Cl.³ .............................................. A45D 7/00
[52] U.S. Cl. .......................................... 132/7; 424/70
[58] Field of Search ................... 132/7; 424/70–72, 424/DIG. 2; 252/544

[56] References Cited

U.S. PATENT DOCUMENTS 3,960,782  6/1976  Daley .................................. 252/544
4,324,263  4/1982  de la Guardia .......................... 132/7

*Primary Examiner*—Gregory E. McNeill
*Attorney, Agent, or Firm*—William H. Needle

[57] ABSTRACT

A composition for forming a second composition to treat hair, and method of treating hair, are disclosed. The first composition is based upon guanidine hydroxide in an inert organic topically acceptable liquid medium which is essentially free of water and carbon dioxide. When the composition is ready for use, water is added thereto to form an aqueous composition which is suitable for use in treating hair to cause the hair to assume a desired configuration.

12 Claims, No Drawings

COMPOSITION AND METHOD FOR HAIR TREATMENT

FIELD OF THE INVENTION

The present invention is directed to compositions suitable for use in the treatment of hair to cause the hair to assume a desired configuration, and to methods of hair treatment. More specifically, the present invention is directed to compositions wherein guanidine hydroxide is the principal active ingredient of the hair treating composition.

BACKGROUND OF THE INVENTION

Commercial products based upon compositions containing thioglycolates, sulfites or alkali metal hydroxides, such as sodium hydroxides, have been widely used to permanently straighten unstraight hair, especially to straighten unstraight Negro hair. Of these products, the thioglycolate compositions and the sulfite compositions which have been commercially marketed have been relatively ineffective, with the hair in many cases reverting at least partially to the original unstraight form. While very effective in producing the desired straightening effect, sodium hydroxide compositions are very harsh to both the scalp and the hair, and the use of such compositions has resulted in numerous instances of scalp irritation and/or burning, and has also resulted in a substantial reduction of the strength of the treated hair, and even, in some instances, considerable hair loss.

Various guanidine compounds have been evaluated by the prior art in hair waving or hair straightening compositions. Of these guanidine thioglycolate appears to have had the most attention by researchers in this art. See, for example, Shansky, *American Perfumer and Cosmetics*, Volume 78, August, 1963, 32–34; Bogaty et al, *American Perfumer and Cosmetics*, Volume 78, November, 1963, pages 45–47; and Shansky, *American Perfumer and Cosmetics*, Volume 78, December, 1963, pages 29–30.

Various organic bases including guanidine have been found to accelerate the dehairing effect of calcium hydroxide suspensions. See, e.g. Barry, "Delipatories" *Cosmetic Science and Technology*, Edited by Balsam and Sagarin, 2nd Edition, Volume 2, Chapter 18, page 39, 45, Wiley Interscience, New York, 1972 and Barry "Depilatories" *Cosmetic Science and Technology*, Edited by Sagarin, First Edition, Chapter 20, page 461–462, Interscience Publishers, New York, 1957, and references cited therein.

U.S. Pat. No. 3,157,578, Nov. 17, 1964, discloses compositions for the permanent waving of human hair utilizing a solution containing, e.g., thioglycollic acid and guanidine carbonate. These compositions are employed in the form of aqueous solutions having a pH value of from 7–9, with the guanidine used to replace ammonia used previously thereto, both to function as a neutralizing agent for the acid reducing agent, and also in the form of ammonium carbonate for pH control.

U.S. Pat. No. 3,861,868 of Jan. 21, 1975 acknowledges, in column 1 thereof, earlier abandoned applications relating to the use of guanidine salts in hair drying compositions and hair bleaching compositions.

British Pat. No. 1,274,565 of May 17, 1972 discloses a process for the straightening of human hair wherein hair straightening is conducted in two separate stages. In the first stage, a known keratin softening substance, such as an alkali hydroxide, sulfite or bisulfite, or a salt of a mercaptocarboxylic acid, is permitted to act upon the hair. After the extensive removal of the keratin softening component, a media containing a swelling substance is applied to the hair. Suitable swelling agents include monovalent aliphatic alcohols, aromatic alcohols, aliphatic diols, ether alcohols, sulfoxides, sulfones, thiocyanates, thiourea and urea, and water-soluble derivatives thereof.

U.S. Pat. No. 3,865,930 of Feb. 11, 1975 discloses a permanent wave composition based on a two-stage operation, wherein in the first stage the S—S linkages of the keratin fiber are opened at an alkaline pH with the addition of a reducing agent such as a thiol. The hair is then treated in a second stage with an oxidizing or neutralizing agent to reconstitute the S—S bridges, so as to impart to the hair the desired configuration. The patent relates to a composition for the aforesaid second stage, wherein the S—S bridges are reformed. This composition is a two-component composition, with one component based on a water-soluble sulfite, bisulfite, metabisulfite, or thiourea, and the other component is hydrogen peroxide.

U.S. Pat. Nos. 2,817,342 of Dec. 24, 1957 and 2,840,086 of June 24, 1958 relate to permanent waving compositions based upon sulfite-type materials. Among other acid sulfites disclosed are an acid solution of guanidine bisulfite, formed by bubbling sulfur dioxide gas into an aqueous solution of guanidine carbonate.

Japanese Pat. No. 76-9013 discloses hair waving or straightening treatments wherein the hair is initially treated with a weak alkali, followed by a treatment with a chelating metallic salt solution. Calcium oxide or calcium hydroxide is used as a chelating agent to prevent mutual interactions of the active ingredients.

U.S. Pat. No. 2,836,543 of May 27, 1954 discloses the use of guanidine as a swelling agent component in a hair setting composition. The composition also includes a water-soluble sulfite and a polyfunctional aromatic additive compound, such as genetistic acid, which acts as an accelerator.

U.S. Pat. No. 3,642,429 of Feb. 15, 1972 is directed to a hair treatment composition based on a polycondensate of methylol compounds and an urein compound. The generic formula for the urein compound appears to encompass guanidine, but guanidine is not named in that patent.

U.S. Pat. No. 3,686,296 is directed to depilatories which are nitrogen-based thioglycerol molecular complexes. The nitrogen base may be, e.g. guanidine or guanidine hydrochloride.

U.S. Pat. No. 3,971,391 of July 27, 1976 is directed to a method of improving the qualities of human hair by converting a part of the cystine links in the hair to lanthioline links. Human hair is treated with certain alkaline and alkali metal hydroxides, and in one embodiment the composition can also include a lanthionization activator. Among various lanthionization activators disclosed is guanidine carbonate (column 4, line 50). The patent is directed to a process for improving hair quality, and not to a hair setting process, with a subsequent setting step being necessary if set hair is desired.

U.S. Pat. No. 2,261,094 of Oct. 28, 1941 is directed to an invention for treating fibrous substances containing keratin, such as wool or hair, wherein a two-step treatment is used. The keratin-containing substances are treated with a reducing agent to affect reduction and disruption of the constituent disulfide or cystine bonds of the keratine, with formation of sulfphydryl groups. Thereafter, the keratin-containing substance, while maintained in the desired form, is treated with a solution of a polyvalent compound, or with an organic compound containing two or more reactive hydrogen atoms, to form sulfur bonds in or between the fiber molecules (note column 1, first column, line 48 through second column, line 6 of the patent). The patentee stresses "it is essential that the treatment with the reducing agent to disrupt the disulfide bonds should proceed as a separate step with the treatment with the polyvalent metal compound or organic compound" (page 1, second column, lines 38 through 42).

U.S. Pat. No. 3,154,470 of Oct. 27, 1964 is directed to a depilatory composition containing four ingredients, namely an emollient base (column 1, lines 41 through 61), water (column 1, lines 62 and 63), a solid basic material (column 1, line 64 through column 2, line 1), and a substitution thiol (column 2, lines 2 through 8). The patent indicates that the substituted thiol is "the essential active depilating agent," note, for instance, column 1, lines 11 and 12, column 2, lines 2 and 3, as well as column 3, lines 66 and 67. The emollient base of the patent serves to provide a protective mantle to prevent skin irritation (note column 2, lines 9 and 10, while the water is emulsified with the emollient base to provide a cream-like consistency to the emollient base (note column 3, lines 61 and 62). The solid basic material, which can be any of guanidine or the alkali and alkaline earth metal hydroxides, carbonates, silicates and tribasic phosphates, functions as "the activating agent for the tioglycolate" (note column 4, lines 15 through 18).

Commonly assigned, copending U.S. application Ser. No. 805,149, filed June 9, 1977 in the name of Mario J. de la Guardia, discloses a composition and process for hair straightening and hair curling. The active hair straightening and curling ingredient of Ser. No. 805,149 is guanidine hydroxide prepared by reacting guanidine carbonate or other suitable guanidine salt with calcium hydroxide or other suitable inorganic hydroxide. Products made in accordance with Ser. No. 805,149 have been on the commercial market in the United States for some while, and have achieved outstanding commercial acceptance. However, because of stability problems, the composition of Ser. No. 805,149 has been marketed as a two-component system, with the guanidine carbonate in one component and the calcium hydroxide in the other component. The guanidine hydroxide in an aqueous guanidine hydroxide solution tends to be converted to guanidine carbonate upon exposure to atmospheric carbon dioxide, so that stability problems arise unless the two components of the system are mixed together and allowed to react, thus forming guanidine hydroxide, only shortly before use. Another disadvantage of Ser. No. 805,149 is that the hair treating composition formed from the two component system commercial product includes calcium carbonate in the composition which is applied to the hair, and the calcium carbonate can lead to complaints of gritty deposits on the hair.

SUMMARY OF THE INVENTION

The present invention is directed to an improvement over the composition described and claimed in Ser. No. 805,149, as in the present invention a single component system may be utilized. The composition consists of guanidine hydroxide in an inert organic liquid medium which is essentially free of water and carbon dioxide. So long as water and carbon dioxide are excluded, the guanidine hydroxide is stable for commercially acceptable lengths of time, so that the need to utilize a two-component system has been obviated.

When the composition consisting of guanidine hydroxide in an inert organic medium is to be used, water is added to the system in an amount of at least 10% by weight, preferably at least 25% by weight, and generally no more than 75% by weight, to form an aqueous composition which is the actual hair treating composition.

DETAILED DESCRIPTION OF THE INVENTION

The composition of the present invention consists essentially of guanidine hydroxide in an inert organic liquid medium which is essentially free of water and carbon dioxide. The guanidine hydroxide can be produced by various methods, and one convenient method is by reaction of a suitable guanidine salt and a suitable hydroxide in an inert organic solvent. The solvent and the reactants should be chosen such that the alkali metal or alkaline earth metal salt produced by the reaction precipitates from the organic solvent, while the guanidine hydroxide remains in solution. Suitable reactants are, for instance, guanidine hydrochloride and potassium hydroxide in an absolute ethanol or isopropanol medium. Equal molar amounts of the guanidine hydrochloride and potassium hydroxide can be combined, and the potassium chloride produced by the reaction has a solubility of only 1 gram in 250 ml of ethanol, so that most of the potassium chloride will precipitate, while guanidine hydroxide is quite soluble in ethanol.

It is absolutely necessary that the guanidine hydroxide be initially prepared in an non-aqueous medium, as if the guanidine hydroxide is prepared in a medium which includes water, the resulting compositions will generally exhibit unsatisfactory stability. Small amounts of residual water will decompose the guanidine hydroxide in the composition.

The preparation of the guanidine hydroxide should be performed under a nitrogen atmosphere, or with other precautions to avoid carbon dioxide absorption. After removal of the potassium chloride or other salt precipitate, the solution of guanidine hydroxide can be concentrated by evaporation on a flash evaporator under reduced pressure. Any storage of the resulting guanidine hydroxide solution should be under nitrogen or other inert gas atmosphere.

Suitable inert organic liquid solvents which can be used in the composition of the present invention include a number of various classes of compounds which, of course, must be acceptable for topical application to human skin. The solvent must be a compound in which guanidine hydroxide is quite soluble and if the guanidine hydroxide is prepared by reaction of a guanidine salt with a suitable hydroxide in the solvent, the solvent should be a good solvent for the guanidine salt. The solvents have other requirements which will be obvious to those in the art, such as, for example, the absence of particularly offensive odors, and the like. The solvent may be an organic compound containing one or more hydroxyl groups, such as, for instance, ethanol, isopropanol, benzyl alcohol, glycerol, propylene glycol, ethylene glycol, and the like. In some instances, the solvent may be one which forms a solid, such as lantrol, stearyl alcohol (mixes with guanidine hydroxide on heating but cools to a solid) and the like. Normally, however, the solvent will be one which remains liquid under ambient conditions. Generally the solvent will contain about 1 to 20 carbon atoms.

In addition to the compounds containing one or more hydroxyl groups, as discussed above, other solvents include dimethyl formamide, acetone, and dimethyl sulfoxide (DMSO), but the latter compound is most unlikely to be used due to rapid absorption through the skin. Polymeric solvents which can be utilized include polyoxyethylene, polyethylene glycol (e.g. of 400 molecular weight) and polypropylene glycol (e.g. of 425 molecular weight). Polyvinyl pyrolidone may be used in some instances, but polyvinyl pyrolidone forms a solid with guanidine hydroxide under ambient conditions (unless a suitable surfactant is used). Ethanol and isopropanol are the preferred solvents.

While methanol can be used as the solvent, it is definitely not preferred in view of its toxicity as compared to ethanol. The preferred alcohols include alkanols of 2 to 18 carbon atoms in length, and aromatic alcohols of 7 to 12 carbon atoms in the molecule thereof. As indicated hereinabove, however, polymeric hydroxyl group containing solvents such as polyethylene glycol and polypropylene glycol can be utilized, and when such polymers are utilized they may function in a dual capacity of being solvent as well as an emollient or thickening agent.

In addition to the alcoholic solvents, amide solvents can also be utilized, such as methylacetamide, dimethylformamide, and the like. In general, the amide solvents will be N-alkyl amides having from 3 to 12 carbon atoms in the chain thereof.

The exact function of the solvent is difficult to determine, as it has not yet been possible to prepare absolutely pure guanidine hydroxide to determine the exact effect of the presence of the organic solvent in the composition of the present invention. However, test results have indicated that greater amounts of ethanol or other organic solvent in the guanidine hydroxide improves the stability of the guanidine hydroxide. This effect could be based on the fact that the removal of greater amounts of ethanol or other organic solvent from the guanidine hydroxide would be concentrating any water present, and also concentrating the guanidine hydroxide itself, or the effect could be an ethanol solvation layer which might serve to protect the guanidine hydroxide from water. For instance, in early stability tests, two compositions based upon guanidine hydroxide and ethanol were prepared, one containing guanidine hydroxide in an amount corresponding to 40% by weight of guanidine, and the other containing guanidine hydroxide in an amount corresponding to 10% by weight of guanidine. The compositions were stored under identical conditions, and analyzed for weight loss of guanidine. The more concentrated composition had a weight loss of 7.5%, with the less concentrated (the 10% guanidine) composition having a weight loss of 6.5% of guanidine. The compositions were also titrated for the amount of guanidine hydroxide therein, and after a one month time interval of storage, the composition containing 40% of guanidine had lost 13.4% of the guanidine hydroxide originally therein, whereas the 10% guanidine concentration composition had lost 6.3 weight % of the guanidine hydroxide originally therein. Generally at least 0.5% of the ethanol or other solvent will be utilized in this composition. Up to about 25% by weight of ethanol can be utilized before the ethanol starts to inhibit the hair treatment by the guanidine hydroxide. Thus the composition contains, as a major component, guanidine hydroxide, together with 0.5 to 25 weight percent of inert organic solvent, and the composition will be more in the nature of a cream or slurry or semi-liquid, rather than a low viscosity solution.

For storage stability the composition of the present invention should be in a container which excludes water and carbon dioxide. So packaged, the compositions of the present invention are in the form of a single component, yet exhibit commercially adequate shelf stability. The container in which the composition of the present invention is packaged should be inert to the container contents, and it is greater preferred that the container be hermetically sealed to exclude water and carbon dioxide. As indicated, the carbon dioxide appears to react with the guanidine hydroxide to produce quanidine carbonate, and the water appears to react with the guanidine hydroxide to produce degradation of the guanidine hydroxide into lower molecular weight compounds, such as ammonia.

After the container containing the composition of the present invention has been opened, however, the composition should be used within a relatively short period of time, and preferably within 48 hours, due to the possibility of guanidine hydroxide in the composition being converted into guanidine carbonate through exposure to atmospheric carbon dioxide. Guanidine carbonate exerts no significant hair treating effect, so that the composition will be rendered essentially unusable upon conversion of an appreciable amount of the guanidine hydroxide into guanidine carbonate.

As the potassium chloride, calcium carbonate, or other precipitated salt is removed from the guanidine hydroxide solution prior to formation of the abovedescribed aqueous composition suitable for application to the hair, no gritty deposits of the salt will be noted on the hair, leading to reduced consumer complaints.

The aqueous composition containing the guanidine hydroxide and the organic solvent should have a concentration of guanidine hydroxide within the range of from about 1% by weight to about 50% by weight, based upon the total weight of the aqueous composition. Concentrations below about 1% by weight are generally too dilute to be effective, and concentrations of guanidine hydroxide above about 50% by weight generally exceed the solubility limit.

It is greatly preferred that the guanidine hydroxide concentration be within the range of 2 to 20% by weight, based on the total weight of the composition to be applied to the hair, and more preferably the guanidine hydroxide concentration is in the range of 3 to 10% by weight. Most preferably the guanidine hydroxide concentration will be from 4 to 7% by weight, based on the total weight of the composition.

While in some instances the water which is added to the solution of guanidine hydroxide and organic solvent may have no other additives therein, it is generally preferable to incorporate emollients therein, in order to protect the scalp and skin of the user. The emollients can be in the form of an anhydrous system, and if inert to guanidine hydroxide can be used in the guanidine hydroxide-inert organic solvent system. Alternatively, the emollients can be incorporated into the water which is added to the composition of the present invention, or the emollients can be added to the composition of the present invention as a separate ingredient. In order to market a composition for hair curling or hair relaxing, with the marketed composition being in a single container, the emollient will normally be included in the guanidine hydroxide composition, so that the end user only needs add tap water to the container contents in order to obtain the hair curling composition of the hair relaxing composition.

The aqueous composition containing guanidine hydroxide may be used for hair curling or hair straightening or relaxing, and for curling applications generally an aqueous composition of lower viscosity will be used, so that the composition has a lotion-like consistency. On the other hand, for relaxing applications, the composition will normally be in the form of an emollient base which has higher viscosity. This difference in viscosity, depending upon use, will be for the reason that for most curling applications the hair treating composition must penetrate layers of hair on a curler, whereas for straightening applications normally the hair to be treated will be simply brushed or combed in order to straighten same during treatment. The relaxing compositions of the present invention exhibit so-called "permanent relaxation," a relaxing effect which lasts until new hair growth requires repetition of the treatment. The compositions exhibit improved hair strength retention and significantly reduced scalp irritation, compared to relaxing compositions based upon alkali metal hydroxide.

The composition is applied to the hair and allowed to remain in contact with the hair for a suitable time, conveniently about 5 to 45 minutes. After the treatment time has elapsed, the composition will be removed from the hair, and it is preferred that the treated hair be fixed or neutralized while the hair is maintained in a substantially straightened configuration. During neutralization the pH value of the hair will be reduced to no greater than about 7, and preferably the pH of the hair is reduced to about 5.0 to 6.5 during neutralization, although lower pH values may be used if desired.

Guanidine hydroxide aqueous compositions have also been found to be surprisingly effective in so-called "permanent wave" applications, wherein the compositions exhibit the advantages of effectiveness, reduced irritability, and high hair strength retention, similar to the advantages exhibited by the hair relaxer compositions of the present invention. In addition, the sulfur dioxide, mercaptan and/or ammonia smell noticed with conventional commercial waving compositions will not be noticed when using the compositions of the present invention.

As noted hereinabove, after the package containing the solution of guanidine hydroxide and organic solvent is opened, it should be used within a short period of time, e.g. within about 48 hours. It is especially important to utilize the guanidine hydroxide composition within a relatively short period of time after the addition of water thereto to form the aqueous guanidine hydroxide composition.

In addition to an emollient, the aqueous guanidine hydroxide composition can contain other conventional additives in order to provide their known functions therein. For instance, the composition may contain an emulsifier, a thickener, and/or a humectant, and preferably is in the form of an aqueous cream. Preservatives may be added, and accelerators may be present, especially if low concentrations of guanidine hydroxide are utilized.

Higher concentrations of guanidine hydroxide in the aqueous relaxer composition raise the possibility of greater scalp irritation and more hair damage. The treatment time can generally be reduced with higher concentrations, so that if adequate care is taken, as may be the case in commercial beauty shop operations, to minimize exposure, such higher concentrations may be utilized.

As applied to the hair, the aqueous guanidine hydroxide relaxer or curling composition of the present invention will not contain any sulfur-based keratin-breaking agents, and preferably the composition does not contain any organic sulfur-containing compounds. While thiourea or similar compounds may be utilized as accelerators, normally this is unnecessary and not preferred.

Normally the aqueous guanidine hydroxide composition will have a pH value above 11.8, preferably about 12.5 to about 13.5, and more preferably around 13.0.

The time of treatment of the hair to be relaxed or curled with the aqueous guanidine hydroxide composition will normally be within the range of 5 to 45 minutes, with the time starting from the first application of the relaxer or curling composition to the hair. Generally this treatment time will be at least 10 minutes, and there is no real upper limit to the time that the composition can remain on the hair, with the above-noted 45 minute time generally being about the greatest length of time that is commercially acceptable to end users. It is greatly preferred to utilize no more than about 30 minutes, and preferably less than 25 minutes, of treatment time, and most preferably the treatment time is in the neighborhood of 20 minutes or so.

After the above treatment time has elapsed, the relaxer composition should be removed from the hair in order to prevent further decrease of the strength retention of the treated hair. A major portion of the relaxer composition can be removed from the hair by thorough rinsing. It is greatly preferred that the rinsing be followed by a neutralizing step, using any suitable neutralizing agent. A buffered neutralizing shampoo has been found to be effective, but any conventional neutralizing methods and compositions well known to the art may be utilized. For instance, citric acid may be added to a conventional shampoo until the pH of the acidified shampoo has been reduced to 5.0 to form an effective neutralizing shampoo. Preferably the hair is neutralized by reducing the pH thereof to a value of no greater than about 7, more preferably to a value of about 5.0–6.5. While lower pH values may be used, it is generally preferred to maintain the pH of the treated hair within the range of about 5.0 to about 7.0.

Generally the aqueous composition will be applied to the hair at ambient temperatures, but the composition may be at a temperature of 35°–140° F. if desired. No advantages will be obtained by working outside of this temperature range.

EXAMPLES OF THE INVENTION

Example 1. An emollient base was prepared using the following formula:

| Relaxer Base | | Wt. % |
|---|---|---|
| (A) | Cyclochem NI | 10.0 |
| | Cetyl Alcohol | 2.0 |
| | Mineral Oil | 20.0 |
| | Propylparaben | 0.05 |
| (B) | Water | 54.80 |
| | Methylparaben | 0.15 |
| | Propylene Glycol | 5.00 |
| | Lantrol AWS | 3.00 |
| (C) | Duponol XL | 5.00 |

| -continued | |
|---|---|
| Relaxer Base | Wt. % |
| | 100.00 |

11 grams of 89.90% by weight guanidine hydroxide in absolute ethanol was mixed with 209 grams of the above relaxer base. After thorough mixing the product had approximately 4.49 weight % of guanidine hydroxide.

Promptly after mixing the composition was applied for 20 minutes to hair of Negro subjects. After 20 minutes had elapsed, the hair was rinsed with water until all of the relaxer composition was removed, and thereafter a neutralizer shampoo, described in Example 1 of Ser. No. 805,149, the disclosure of which is hereby incorporated by reference, was applied. The hair was then dried and set. The hair after drying was in the relaxed condition, with a soft and glossy appearance. The subject did not complain of burning or irritation, even though the pH of the product was 13.2

The Lantrol AWS used in this example was a polyethylene glycol derivative of lanolin oil with an average of 75 mols of ethylene oxide units. This product is also known as PEG-75 Lanolin Oil.

Example 2. Example 1 was repeated, except the guanidine hydroxide was in isopropyl alcohol solvent. 12 grams of 82.70% guanidine hydroxide isopropyl alcohol was mixed with 208 grams of the relaxer emollient base of Example 1, to produce a product having approximately 4.49% of guanidine hydroxide.

After similar application to the hair of Negro subjects, the composition produced relaxed hair which was similar in appearance and other results to that of Example 1.

What is claimed is:

1. A composition for treating hair when applied thereto, comprising a non-aqueous solution of guanidine hydroxide and from 0.5% to 25% by weight of said solution of an inert organic solvent for said guanidine hydroxide, the user adding a preselected amount of water to said solution before applying said composition to the hair, said composition having a pH greater than 11.8.

2. A composition as claimed in claim 1 wherein said solvent contains a hydroxyl group.

3. A composition as claimed in claim 2 wherein said solvent is an alkanol having from 2 to 18 carbon atoms.

4. A composition as claimed in claim 2 wherein said solvent is an aromatic alcohol having from 7 to 12 carbon atoms.

5. A composition as claimed in claim 1 wherein said solvent is ethanol.

6. A composition as claimed in claim 1 wherein said solvent is isopropanol.

7. A composition as claimed in claim 1 wherein said solvent is an N-alkyl amide having from 3 to 12 carbon atoms.

8. A manufacture for use in treating hair comprising a container of a non-aqueous composition of guanidine hydroxide and an alcohol having from 2 to 18 carbon atoms to which an effective amount of water is added to form a preparation having a pH of at least 11.8 which is applied to the hair.

9. A manufacture as claimed in claim 8 wherein said alcohol is ethanol.

10. A manufacture as claimed in claim 8 wherein said alcohol is isopropanol.

11. A method of treating hair, comprising the steps of:
(a) providing a non-aqueous composition comprising guanidine hydroxide and from 0.5% to 25% by weight of said composition of an inert organic solvent;
(b) mixing an effective amount of water with said composition to form a mixture, the pH of said mixture being at least 11.8;
(c) applying said mixture to the hair for a preselected period of time; and
(d) removing said mixture from the hair.

12. The method as claimed in claim 11 wherein said solvent is ethanol.

* * * * *